United States Patent [19]
Schwind

[11] Patent Number: 5,779,723
[45] Date of Patent: Jul. 14, 1998

[54] DEVICE FOR CORNEAL SURGERY

[75] Inventor: Herbert Schwind, Kleinostheim, Germany

[73] Assignee: Herbert Schwind GmbH & Co. KG, Kleinostheim, Germany

[21] Appl. No.: 738,582

[22] Filed: Oct. 29, 1996

[30] Foreign Application Priority Data

Oct. 30, 1995 [DE] Germany ............... 195 40 439.4

[51] Int. Cl.$^6$ .......................................... A61F 9/00
[52] U.S. Cl. ............................. 606/166; 606/167
[58] Field of Search ................. 606/1, 107, 166, 606/167, 170, 185; 604/19, 22

[56] References Cited

U.S. PATENT DOCUMENTS

| | | |
|---|---|---|
| 4,662,370 | 5/1987 | Hoffmann et al. . |
| 4,674,503 | 6/1987 | Peyman et al. . |
| 4,840,175 | 6/1989 | Peyman . |
| 4,903,695 | 2/1990 | Warner et al. . |
| 5,133,726 | 7/1992 | Ruiz et al. . |
| 5,312,394 | 5/1994 | Beckman . |
| 5,496,339 | 3/1996 | Koepnick ..................... 606/166 |
| 5,586,980 | 12/1996 | Kremer et al. . |
| 5,643,299 | 7/1997 | Bair ............................. 606/166 |

FOREIGN PATENT DOCUMENTS

| | | | |
|---|---|---|---|
| 3433581 | 3/1986 | Germany | ..... 606/166 |
| 3433581 | 8/1986 | Germany . | |
| 3825587A1 | 2/1990 | Germany . | |
| 93/09738 | 5/1993 | WIPO . | |
| 94/01067 | 1/1994 | WIPO . | |

*Primary Examiner*—Glenn K. Dawson
*Attorney, Agent, or Firm*—Evenson, McKeown, Edwards & Lenahan, PLLC

[57] ABSTRACT

A device for corneal surgery includes an oscillating blade which, during a cutting process, separates a corneal lamella. The movement of the blade is stopped at a certain place so that the separated corneal lamella remains attached by a tissue hinge to the corneal tissue which has remained on the eye.

23 Claims, 4 Drawing Sheets

DEVICE FOR CORNEAL SURGERY

BACKGROUND OF THE INVENTION

The invention concerns a device such as that known from German Patent No. 3,433,581 (which corresponds to U.S. Pat. No. 4,662,370). In such a device, a base ring, which can be attached by negative pressure, is placed over the eye to be treated. On the base ring, a support is guided over the eye. The support contains an oscillating knife, the oscillatory cutting of which is at an angle with respect to the direction of advance of the support. In this process, for the purpose of refractive keratotomy, the radius of curvature of the cornea of the eye of the patient is decreased or increased to a predetermined shape by completely cutting the corneal lamella along a cutting line and removing it from the eye. The remaining cornea, after this cut, presents the desired curvature for the refractive vision correction. The desired curvature is realized by an applanation surface which is placed on the corneal surface and shaped accordingly. The drawback which must be accepted is that in order to effect vision correction, a cut with a relatively large surface is performed on the cornea, and the cut surface remains permanently.

Furthermore, it is known how, after the complete removal of the corneal lamella, to carry out corrections using laser beams at the exposed tissue of the cornea, and to replace the separated corneal lamella on the eye (U.S. Pat. No. 4,840,175). The exact replacement of the removed corneal lamella on the treated eye places high demands on the skill of the surgeon. Moreover, it is practically impossible to replace the removed corneal lamella on the cornea with the exact alignment that it had on the eye before it was removed.

SUMMARY OF THE INVENTION

The object of the invention is to produce a device of the type mentioned in the introduction with which the conditions existing prior to the corneal treatment can be reestablished simply at the corneal surface after the corneal treatment.

By stopping the progress of the knife during the cutting process at a certain point in the device, it is achieved that the entire corneal lamella is not removed from the eye. The separated corneal lamella, according to the invention, is connected to the cornea which remains on the eye by means of a hinge formed of corneal tissue. The corneal lamella can be folded away from the corneal skin surface so that the stroma is exposed, for a laser treatment, for example.

During the return stroke of the support, which carries the cutting device, it is preferred that the base ring remains attached to the eye with negative pressure. It is also preferred that, during the return stroke of the support and the cutting device, the negative pressure in the ring chamber is maintained in the area of the cornea, so that a problem-free attachment of the separated corneal lamella is effected during the return stroke of the cutting device, particularly the cutting edge. The drive for the oscillation knife movement is switched off during the return stroke. From U.S. Pat. No. 5,133,726, a cutting device is known in which the drive of the oscillating knife and the drive of the support are coupled, so that a separate control of the drives is not possible. This would be disadvantageous particularly during the return stroke of the cutting device, during which, according to the invention, the knife movement must be cut off. As soon as the return stroke is finished, the negative pressure generator is switched off, so that the cutting device can be removed from the eye and a subsequent treatment can be carried out, particularly of the stroma, after the folding away of the corneal lamella about the remaining hinge site.

It is therefore preferred that the center of the base ring, on which the knife is guided by a movable support, can be moved in the beam path of a laser beam directed onto the eye of the patient. In this manner it is possible to combine a combination of the cutting device with an apparatus to carry out a laser ablation on the cornea of the eye, such that the corneal lamella is, partially away from the hinge site, separated from the eye and folded back. After the removal of the cutting device from the eye, the laser beam is directed onto the exposed stroma of the cornea of the eye. The desired refractive correction can then be carried out on the eye. After the laser treatment, the corneal lamella, which had been folded away, is folded back onto the treated stroma, where the lamella which has been folded back returns, because of the hinge, to the position in which it was before the operation. This is important because the surface of the cornea of the eye does not form an exact spherical cap. For an exact refractive correction, it is therefore necessary that the separated corneal lamella is returned to the eye with the same positioning as before the separation. The subsequent attachment of the folded back cornea, for example, with sutures, which is required in the case of complete separation of the corneal lamella, is not necessary here. Moreover, the growth of the tissue of the separated lamella part as it becomes again attached to the tissue remaining on the eye, occurs without transition, and without scar formation.

Two separate drives are provided for the oscillatory knife movement and for the forward and return movement of the support. The knife is driven through a separate shaft, and the support is also driven through a separate shaft. Each of the two shafts is driven by an associated motor. As a result, it is ensured that the oscillatory drive for the knife and the drive for the forward and return movement of the support, and thus the forward and return movement of the oscillating knife, which is located in the support, can be controlled separately. It is preferred that the two motors are connected by flexible shafts to the support and to the knife. Thus, it is ensured that the cutting instrument can be moved in the beam path of a laser ablation apparatus for corneal treatment, before the laser treatment can be carried out on the eye of the patient. The patient need does not change his or her position for the treatment. The cutting treatment can therefore be carried out on the eye of the patient, which is located under the radiation optics of the laser apparatus, and the cutting apparatus can be removed after the cutting process. However, it is also possible for the two motors to be provided in the form of micromotors directly at the cutting apparatus.

Because of the separate drives for the support movement (forward movement and return movement) and for the oscillation knife movement, the drive of the support forward movement can be controlled in such a manner that a stop is effected whenever the oscillation knife movement is at the corresponding reversal point of the direction of motion (speed=0). As a result, the forward movement of the knife stops for each stop of the knife movement during which no cutting occurs.

A piezoelectric linear drive, which is preferably brace supported at the base ring, is suitable as an inertia-free working drive device for the support forward movement. This piezoelectric drive can be designed in the usual manner (for example, German Pat. No. 3,825,587) and it can consist of piezo-actuators. For example, three piezo-actuators can be provided. A suitable piezo-drive consists of three piezo-crystals, whose movement and the linear movement of the support drive, which is coupled to it, can be explained by analogy with the movement of an inchworm. The front and back piezo-crystals, which may be in the form of clamp actuators, serve as brakes and the middle piezo-crystal, for example, in the form of a forward movement actuator, is used for imparting movement. The piezo-crystals, in particular piezo-ceramics, which are located in a housing that is connected to the support in this process, move forward on a support, particularly a metal band or rail, which is directly or indirectly connected to the base ring. The first piezo-crystal holds the base, while the second piezo-crystal (middle piezo-crystal) expands. To allow movement of the arrangement, the second brake formed by the third piezo-crystal is open. After the expansion, the third piezo-crystal is clamped rigidly to the base, particularly the metal band, that is, the second brake is closed, while the first brake, that is, the first piezo-crystal opens and the second piezo-crystal (middle piezo-crystal) pulls together. The process then repeats. The drive motion can also be reversed. The housing is directly or indirectly connected to the base ring, and the base, for example, the metal band, moves and is connected to the support.

The oscillation knife movement can also be generated by a crystal oscillator. In that case, it is not necessary to couple the oscillating knife and the support which is to be driven linearly via flexible shafts connected to the motors. Both drives can then be provided directly at the cutting apparatus.

BRIEF DESCRIPTION OF THE DRAWINGS

The invention is further explained with reference to the figures.

DESCRIPTION OF THE PREFERRED EMBODIMENT

Figure 5:
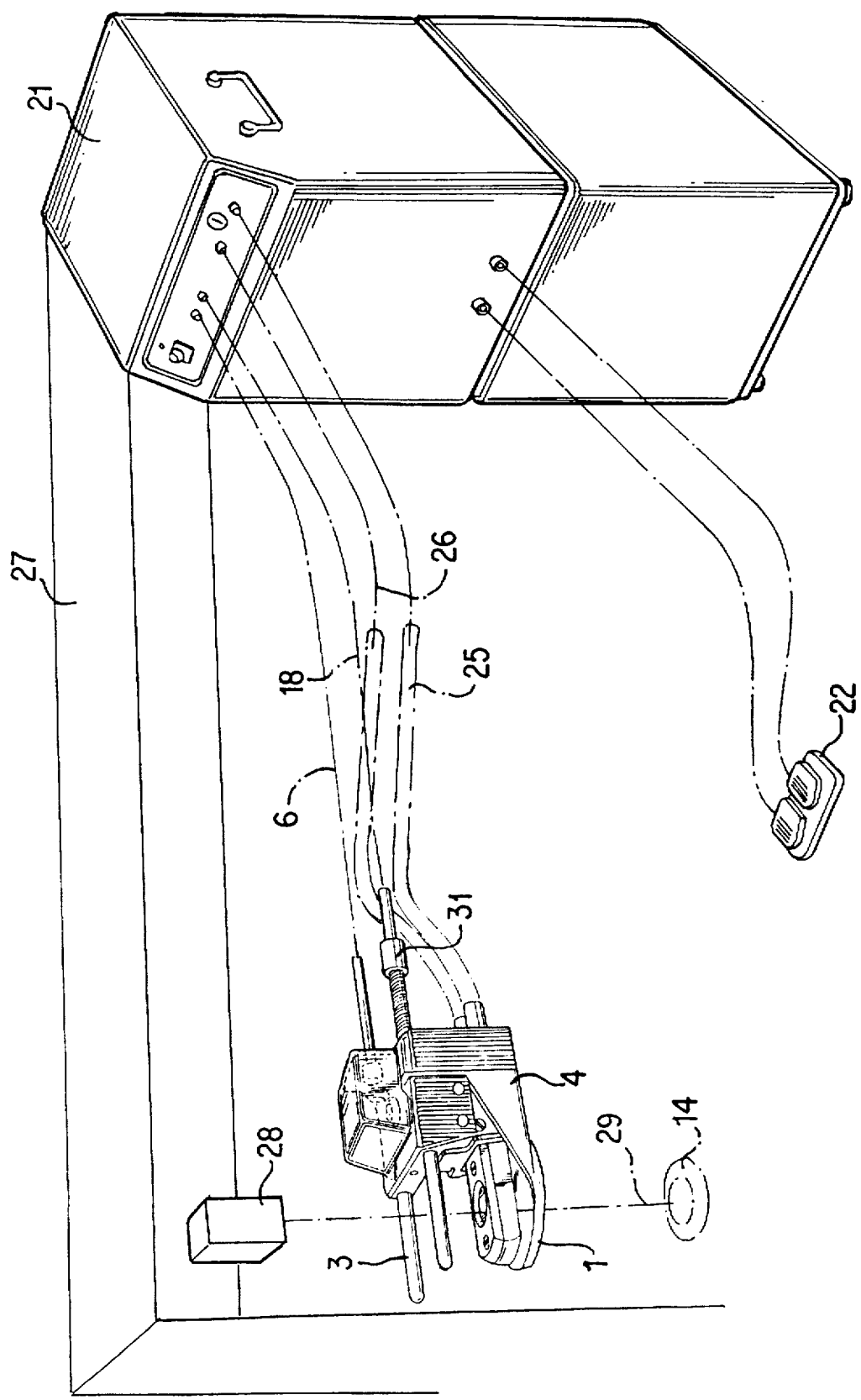
FIG. 5 is an embodiment example in which the cutting apparatus according to FIGS. 1 and 3 is combined with a laser apparatus to perform surgical interventions on the cornea of the eye.

The example of a cutting apparatus represented in the figures has a base ring 1, which can be placed over the eye 14 of the patient (FIG. 5). A support guide, in the form of two cylindrical guide rods 3, is located over base ring 1 in a frame which is rigidly connected to the base ring 1. The guide rods 3 extend in the forward and return movement direction of the support 2. In support 2, the knife in the form of a blade 11 is placed so that it can oscillate. The blade 11 undergoes an oscillatory movement diagonally (vertically) with respect to the forward and return movement direction (double arrow 15) of the support. During the cutting process, the blade 11 is led in a blade guide 16 on a frame 4 which is connected to the base ring 1.

A first drive shaft 5 is provided for the forward and return movement of the support and the blade 11 located therein. The drive shaft 5 has external threads, which engage corresponding internal threads of the support 2 for the forward and return movement.

For the oscillating drive of the blade 11, a second drive shaft 6 is provided, which presents a bevel gear 17 at its front end that engages with a second bevel gear 7 and that generates, in a known manner, the oscillation movement of the blade by means of a drive which is not represented in greater detail, for example, as in German Patent No. 3,433,581, with the aid of a rotating cam.

The first shaft 5 is connected by a flexible transmission line 18 to an associated first drive motor. The second drive shaft 6 is also connected by a flexible transmission line to a second drive motor. The two motors can be housed in a central housing 21. This central housing can also contain the control device for other components which are of importance in the corneal treatment on eye 14 of the patient. For example, a foot switch 22 for switching certain components on and off, for example, for controlling the support forward movement and the support return movement, can be connected to the central control device located in the housing 21.

Figure 1:
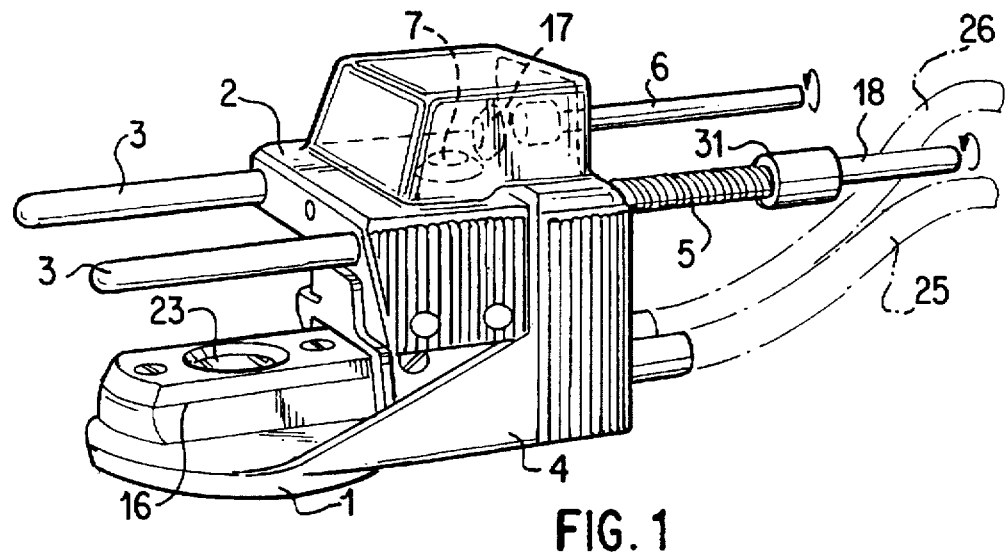
FIG. 1 is an embodiment example in a perspective view.
Figure 2:
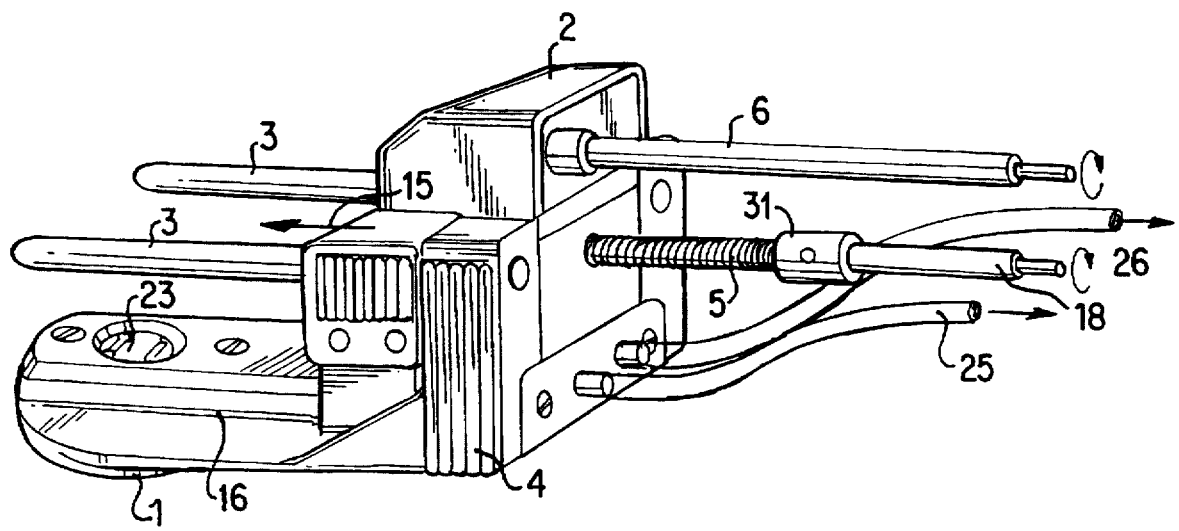
FIG. 2 is the embodiment example in another perspective view.
Figure 3:
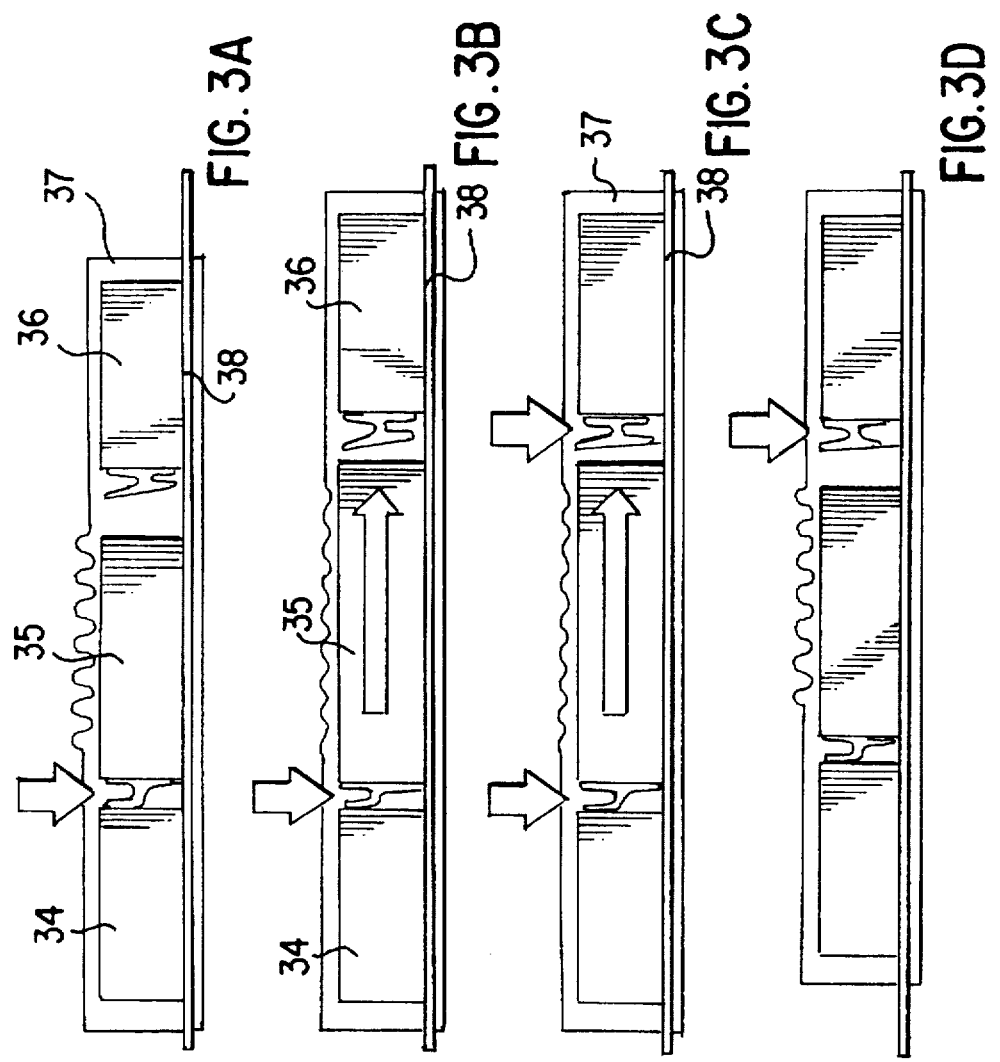
FIG. 3 is an embodiment example of a piezo-drive.

FIG. 3 is an embodiment example of a piezo-drive, particularly a linear drive, for the support. This linear drive consists of three piezo-crystals 34, 35 and 36. The front and back piezo-crystals 34 and 36 serve as brakes, and the middle piezo-crystal 35 is used for imparting movement. The three crystals are arranged in a housing 37, which is connected to the support. The movement occurs on a base 38, which can be in the form of a band or rail, and which is directly or indirectly rigidly connected to the base ring 1. For example, one of the two rails 3 can serve as a base. As a result, the linear shift of the support 2 with respect to the base ring 1 is achieved.

During the movement of the housing 37 and the support 2 which is connected to the housing, the first piezo-crystal 34 is rigidly connected to the base 38, for example, by clamping, and it functions as an immobilizing brake. The second piezo-crystal 35 expands from the position shown in representation (A) to the position shown in representation (B), where the third piezo-crystal 36 is separated from the base 38, so that a shift occurs in the positions shown in representations (B) and (C). After the expansion of the second piezo-crystal 35 to the position shown in representation (C), the piezo-crystal 37 is rigidly connected to the base 38, while the first piezo-crystal 34 is opened and it can then also move during the pulling together of a second piezo-crystal 35. The three crystals are then moved forward from the initial position shown in representation (A) to the position shown in representation (D), and during this process the support which is connected to the housing 37 has also been moved with respect to the base 38 and thus with respect to the base ring 1. The sequence of movements is then repeated in a next step.

To allow movement in a manner of an inchworm, the housing 37 is constructed in a flexible manner, particularly in the area of the second piezo-crystal 35. To control the brake function of the front and back piezo-crystal and for the contraction and expansion of the second piezo-crystals in the direction of movement, known control means are used, and are represented in German Patent No. 3,825,587, for example.

Of course, it is also possible to connect the housing 37 to the base ring and the bases 38 to the support, so that the reversal of motion achieves the same linear movement for the support. During the return stroke of the support, the sequences of movement are produced in reversed order by the appropriate control of the piezo-crystals.

Figure 4:
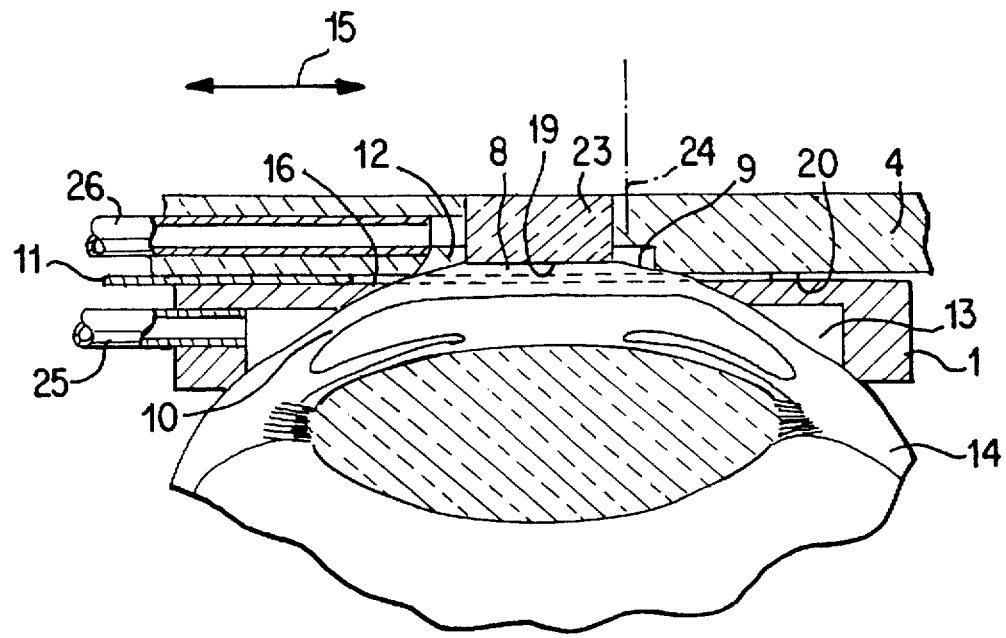
FIG. 4 is a cross-sectional representation to explain the cutting process.
Figure 6:
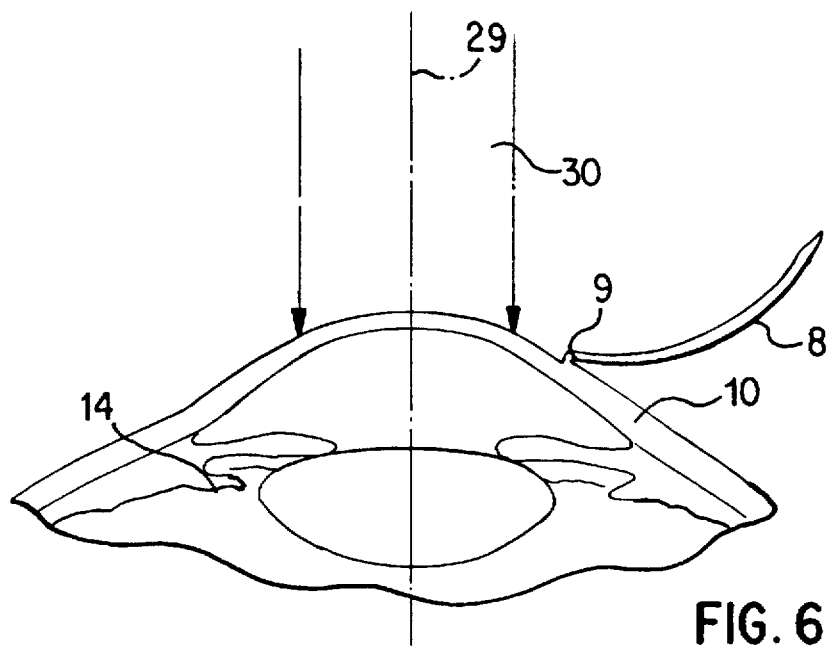
FIG. 6 is a diagrammatic representation of the corneal treatment after the cut.

FIG. 4 is a cross-sectional representation of the cutting apparatus placed over the eye 14 of the patient. The base ring 1 is applied to the surface of the eye, and in the area of the eye bulb, an annular chamber 13 is formed between the base ring 1 and the surface of the eye, which is connected through a pressure-sealed pipe 25 to an apparatus for the generation of a negative pressure which is not represented in further detail. Furthermore, an annular chamber 12 is formed in the area of the cornea, which is connected by a pressure-sealed pipe 26 to an apparatus for the generation of a negative pressure. The apparatuses for negative pressure generation can also be housed in the housing 21. The blade guide 16 is located between the base ring 1 and the frame 4. During the forward movement, the blade 11 in FIG. 4 moves from left to right in the guide 16. The cutting plane is located in the hollow space of guide 16, in which a corneal lamella 8 is separated from the eye while maintaining a tissue hinge 9 (FIG. 6). As a result of the negative pressure in the annular chamber 12, the corneal lamella to be separated is always fixed exactly during the cutting process. An inspection glass 23 is located at the frame 4, above the corneal lamella 8 which has been partially separated by a cut. The inspection glass 23 can contain cross hairs, so that an exact alignment of the cutting apparatus with a mark that has been placed on the eye before the cutting process can be achieved.

On a part of the frame 4 which is located above the blade guide 16, a flat surface 20 is provided at the bottom side. This surface limits the blade guide toward the top. The inspection glass 23 also has a flat surface 19 at its bottom side. This flat surface 19 is shifted towards the top with respect to the flat surface 20 at the frame part 4 so that the desired cutting depths, measured from the tip of the cornea vertically into the corneal tissue, can be set for the corneal lamella. The flat surface 19 at the bottom side of the inspection glass 23 is parallel to the two flat surfaces on the base ring 1 and on the frame part 4, which limit the blade guide 16. The thickness of the corneal lamella 8, which is to be separated and which is kept in flattened form under the flat surface of the inspection glass 23, can be set exactly. It is preferred to use a cutting depth of 150 μm. During the cutting process it is advantageous always to stop the forward movement of the support, and thus the knife, when the back and forth movement of the knife is at a reversal point (speed=0).

A location is provided in the path of forward motion of the blade 11, where the forward motion of the blade or of the support is stopped. In FIG. 4 this place is identified by reference numeral 24. The location 24 which marks a movement stop in the forward movement of the blade or support is arranged and fixed with respect to the eye to be treated 14 in such a manner that as a result of the cutting process, the corneal lamella 8, which is delimited from the cutting plane in the blade guide 16, is not completely separated; instead, it remains connected by the tissue hinge 9 with the cornea 10 which remains on the eye.

By an opening provided in the base ring 1, through which the cornea extends, a treatment zone with a certain diameter, preferably 9 mm, is defined. This is the diameter of the treatment zone which is located in the plane of the blade guide 16. The corneal lamella 8, which extends above this plane, is partially separated during the cutting process from the eye, where, as already explained, the cutting process is stopped at the movement stop location 24, so that the separated corneal lamella remains connected to the eye by the tissue hinge 9.

To carry out the cutting process, the cutting apparatus with base ring 1 is placed over the eye and is fixed by the generation of a negative pressure in chamber 13. A negative pressure for fixation is also generated in the area of the cornea in the annular chamber 12. In this manner, the cutting apparatus is fixed on the eye exactly in the desired position. The switching on of the negative pressure generating apparatus can be done, for example, using the foot switch 22. For example, an acoustic signal can be used to indicate to the operating personnel that the desired negative pressure in the annular chambers 12 and 13 is present. The pumps used for this purpose are capable of generating a pressure of 0–1 bar in the chambers.

For the cutting process, the two drive motors are switched on so that the blade undergoes an oscillatory movement perpendicularly to the plane of FIG. 4 and a forward movement from left to right in FIG. 4. In this process, the corneal lamella 8, which extends above the plane of the blade guide 16, is separated, but, as already explained, the cutting process is ended by stopping the forward motion of the blade at place 24.

The support 2 and the blade 11 are then retracted; however, the corneal lamella 8, which has been separated up to the tissue hinge 9, is maintained fixed as a result of the negative pressure in the annular chamber 12. The base ring 1 also remains fixed to the eye as a result of the negative pressure generated in the chamber 13. At the time of the retraction of the blade 11, the drive for the oscillatory cutting movement is switched off. This can take place by switching off the motor which is associated with the oscillatory cutting movement or by the separation of a coupling, not represented in detail, between the motor and the drive shaft 6. The return movement of the support and the blade 11 is transmitted by the drive of the other motor assigned to the stroke movement. The drive spindle 5 then turns in the direction of rotation which is opposite to that of the forward movement direction.

The oscillatory blade movement of the blade can then be ended or switched off when the blade has reached the movement stop location 24. This movement stop place can be established electronically by a corresponding control and stopping of the motor assigned to the stroke movement in the central control device. This location is determined after the cutting apparatus has been placed in the desired position over the eye. In addition, a solid abutment can be provided between the frame 4 and the support 2 to ensure the movement stop location 24. Furthermore, a coupling part 31, between the drive spindle 5 and the flexible transmission line 18, can function as a final abutment.

After switching off the negative pressure generation apparatus, the cutting apparatus is removed from the eye.

During the cutting process, the oscillation speed of the blade is 1350 rpm. The forward movement speed of the blade is 1.3 mm/sec. The return stroke speed with switched off oscillatory movement is 3 mm/sec. The two separate motors make it possible to control the oscillatory movement and the forward and return stroke movement separately. By using the two cylindrical guide rods 3, an exact guiding of the blade 11 on base ring 1 and on frame 4 is ensured.

As can be seen particularly in FIG. 5, the base ring 1 can be placed exactly over the cornea 10 by placing its center using the cross hairs provided in the inspection glass 23, and then the base ring is fixed at that place using the negative-pressure chambers 12 and 13. In this way it is possible to ensure that the cutting device is placed in the area of the beam path of a laser beam which is to be directed onto the eye after the cutting process. Because of the flexible construction of the drive shafts (flexible shaft part 18 and flexible shaft 6), which are connected to the drive motors that are rigidly mounted in the housing 21, the cutting device can be placed unimpeded in the desired position in the laser treatment installation 27 and again be removed from it. The housing 21, with the control devices located therein, can be integrated in the laser treatment installation 27 for corneal treatment. In this installation, the patient, as is known, is placed on a bed, not illustrated in detail, with his or her eye 14 to be treated located under an irradiation optical system 28. By the irradiation optical system 28, a laser beam 30 is directed onto the eye 14 to be treated along a locating line 29. In the case of a combination of the cutting apparatus with the installation 27, this takes place after the performance of the cutting process and after the partially-separated corneal lamella 8 has been folded back about the hinge site 9 and, as shown in FIG. 6, the laser radiation 30 can be directed onto the exposed stroma. Using laser radiation, it is then possible to perform the desired refractive corrections on the eye 14. After the laser beam treatment, the corneal lamella 8, which is folded back, is again brought into its initial position on the cornea 10, which position exactly corresponds to the position on the eye before treatment.

What is claimed is:

1. A device for corneal surgery comprising:

a base ring which is to be applied to an eye to be treated and fixed by negative pressure which can be generated in an annular chamber in an area of the cornea, an oscillating knife which can be moved over the eye by a support mounted to and guided on the base ring, said oscillating knife being operatively connected to said support a first drive connected to said support for providing movement of the support, a second drive interconnected with said knife for providing oscillatory movement of the knife, the first and the second drives being independently controllable, and a movement stop for stopping forward movement of the support during cutting a lamellar corneal part which is separated from the cornea is connected to the cornea which has remained on the eye by a hinge site formed by corneal tissue so that a separated lamellar corneal piece can be folded laterally away, exposing the eye tissue located below it, and so that during a return stroke of the support, the second drive for providing the oscillatory movement of the knife is stopped by the movement stop.

2. Device according to claim 1, characterized in that the base ring is adapted to remain fixed by negative pressure to the eye during the return stroke of the support.

3. Device according to claim 1, characterized in that the device is adapted to maintain negative pressure in the annular chamber in the area of the cornea during the return stroke of the support.

4. Device according to claim 1, characterized in that the first drive for providing the movement of the support is stopped every time at reversal points of the oscillatory knife movement.

5. Device according to claim 1, characterized in that designated motors are provided for each of the drives.

6. Device according to claim 1, characterized in that the base ring can be lifted off the eye after switching off the negative pressure.

7. Device according to claim 1, characterized in that the movement stop is arranged in such a manner that the corneal tissue has a thickness of approximately 0.3 mm at the hinge site.

8. Device according to claim 1, and further comprising a frame connected to said base ring, characterized in that the movement stop is ensured by a solid abutment between the frame and the support.

9. Device according to claim 1, characterized in that the device is configured to produce a perpendicular cutting depth into the cornea in such that the stroma is exposed.

10. Device according to claim 1, and further comprising an inspection glass extending above and parallel to a cutting plane of the knife.

11. Device according to claim 1, characterized in that the first drive includes a first drive shaft and the second drive includes a second drive shaft.

12. Device according to claim 11, characterized in that the first drive shaft is driven by a first motor and the second drive shaft is driven by a second motor.

13. Device according to claim 11, characterized in that the drive shafts are made of flexible material.

14. Device according to claim 12, and further comprising a central housing in which the motors are arranged separately from the oscillating knife and the support, and flexible transmission lines interconnecting said motors and the drive shafts.

15. Device according to claim 1, characterized in that the first and second drives are located on said base ring.

16. Device according to claim 1, characterized in that the first drive is a piezoelectric linear drive.

17. Device according to claim 16, characterized in that the piezoelectric linear drive is supported at the base ring.

18. Device according to claim 15, characterized in that the second drive is an oscillating crystal which generates the oscillatory movement of the knife and is held by the support.

19. Device according to claim 1, characterized in that the base ring is combined with the support which is guided on top of base ring with a laser ablation apparatus in such a manner that the base ring can be moved with its center in an area in which a path of a laser beam of said laser ablation apparatus is located, which beam is adapted to be directed onto an exposed stroma during laser ablation.

20. A method for performing corneal surgery on one eye comprising the steps of:

fixing a cutting device, which presents an oscillating knife, on the eye;

guiding the oscillating knife, during its cutting movement, perpendicularly to its oscillatory movement in a cutting direction;

separating a corneal lamella, during the cutting movement of the knife, from the cornea of the eye;

stopping the cutting movement at a place where a lamellar corneal piece which has been separated from the eye remains attached to the cornea which has remained on the eye by a hinge site formed by corneal tissue;

ending the oscillatory knife movement and retracting the knife in a direction opposite to the cutting movement;

removing the cutting device from the eye;

folding the lamellar corneal piece away around the hinge site so that a corneal surface located under the lamellar corneal piece is exposed;

treating the exposed corneal surface with laser radiation; and folding the lamellar corneal piece back around the hinge site after laser treatment.

21. A method according to claim 20, and further comprising the step of stopping, at each reversal point of oscillatory knife movement, advance movement of the knife.

22. A method according to claim 20, and further comprising the step of carrying out an ablation by laser treatment at the exposed corneal surface which, after folding the lamellar corneal piece back around the hinge site, results in a refractive correction of the vision of the eye.

23. A method according to claim 22, and further comprising the step of measuring, during cutting, the cutting depth with the stroma of the cornea exposed, wherein the step of carrying out the ablation is performed with the stroma exposed.

* * * * *